United States Patent
Hell

(10) Patent No.: US 8,263,809 B2
(45) Date of Patent: Sep. 11, 2012

(54) PREPARATION OF 3-[(1R,2R)-3-(DIMETHYLAMINO)-1ETHYL-2-METHYLPROPYL]PHENOL

(75) Inventor: Wolfgang Hell, Aachen (DE)

(73) Assignee: Gruenenthal GmbH, Aachen (DE)

( * ) Notice: Subject to any disclaimer, the term of this patent is extended or adjusted under 35 U.S.C. 154(b) by 413 days.

(21) Appl. No.: 12/374,910

(22) PCT Filed: Jul. 23, 2007

(86) PCT No.: PCT/EP2007/006514
§ 371 (c)(1),
(2), (4) Date: Jan. 23, 2009

(87) PCT Pub. No.: WO2008/012046
PCT Pub. Date: Jan. 31, 2008

(65) Prior Publication Data
US 2009/0326271 A1 Dec. 31, 2009

(30) Foreign Application Priority Data
Jul. 24, 2006 (EP) .................................... 06015317

(51) Int. Cl.
*C07C 215/00* (2006.01)

(52) U.S. Cl. ........ 564/443; 564/355; 564/356; 564/374; 514/652; 514/533; 514/345

(58) Field of Classification Search ................... None
See application file for complete search history.

(56) References Cited

U.S. PATENT DOCUMENTS

| 6,248,737 B1 * | 6/2001 | Buschmann et al. ...... 514/231.8 |
| 2006/0167318 A1 | 7/2006 | Jagusch et al. |
| 2006/0194988 A1 | 8/2006 | Hell et al. |

FOREIGN PATENT DOCUMENTS

| EP | 0 693 475 A1 | 1/1996 |
| RU | 2 150 465 C1 | 7/1995 |
| WO | WO 2004/108658 A1 | 12/2004 |
| WO | WO 2005/000788 A1 | 1/2005 |

OTHER PUBLICATIONS

International Search Report dated Oct. 11, 2007 (Two (2) pages).
Hiyama et al., A Facile Route to (±)-2-Arylpropanoic Acids, Sagami Chemical Research Center, Aug. 1986, pp. 645-647.

* cited by examiner

*Primary Examiner* — Sudhakar Katakam
(74) *Attorney, Agent, or Firm* — Crowell & Moring LLP

(57) ABSTRACT

The present invention relates to an improved process for the preparation of 3-[(1R,2R)-3-(dimethylamino)-1-ethyl-2-methylpropyl]phenol monohydrochloride.

15 Claims, No Drawings

PREPARATION OF 3-[(1R,2R)-3-(DIMETHYLAMINO)-1ETHYL-2-METHYLPROPYL]PHENOL

The present invention relates to an improved process for the preparation of 3-[(1R,2R)-3-(dimethylamino)-1-ethyl-2-methylpropyl]phenol monohydrochloride Tapentadol is the INN (International Non-proprietary Name) of 3-[(1R,2R)-3-(dimethylamino)-1-ethyl-2-methylpropyl]phenol monohydrochloride which compound is represented by the formula:

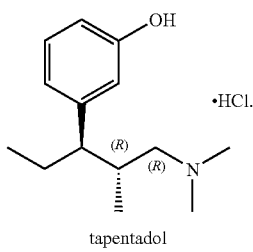

tapentadol

The chemical structure of tapentadol has been disclosed in EP-A-0,693,475 as compound (+21). The synthesis of tapentadol is described in Example 1 and Example 24 steps 1 to 3 and is outlined below using the compound numbers as mentioned in said EP-A-0,693,475.

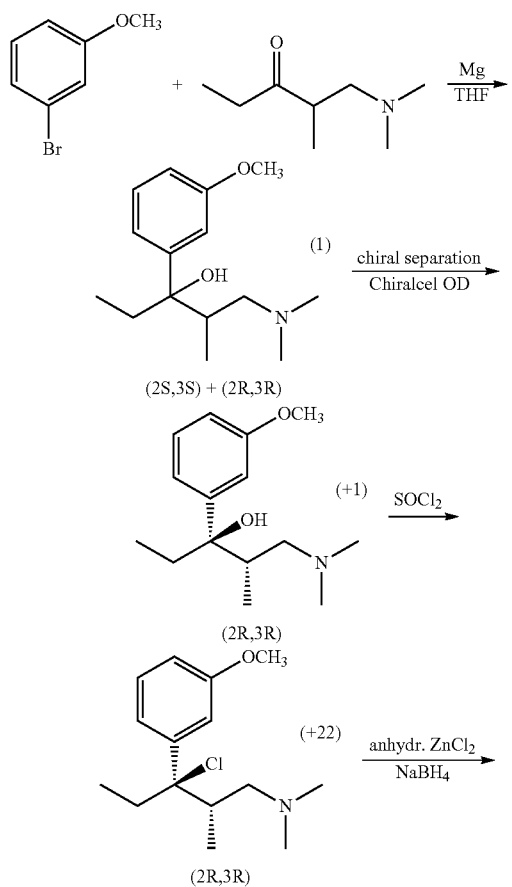

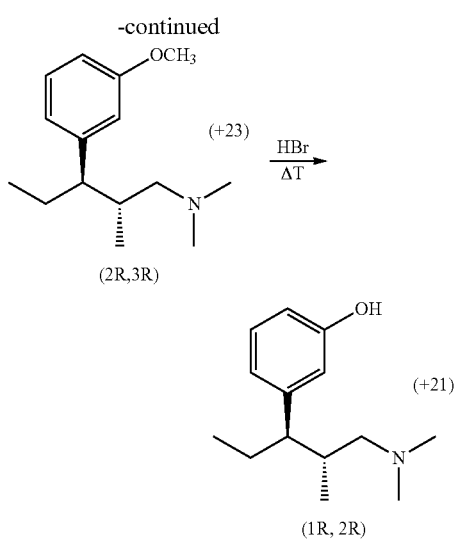

The synthetic precursor of tapentadol in the above scheme is (2R,3R)-3-(3-methoxyphenyl)-N,N,2-trimethylpentanamine (intermediate (+23) in the above scheme) which can be obtained by removing the tertiary hydroxy group of (2S,3R)-1-(dimethylamino)-3-(3-methoxyphenyl)-2-methyl-3-pentanol by consecutive conversion into the corresponding halogenide with thionyl chloride and subsequent removal of the Cl by treatment with zinc borohydride, zinc cyanoborohydride and/or tin cyanoborohydride.

This procedure has the disadvantage that the halogenide compound is prepared using an excess amount of thionyl chloride which is an aggressive chlorinating agent. Moreover the hydrogenation reagents such as zinc borohydride, zinc cyanoborohydride and tin cyanoborohydride present a considerable fire and health danger when used on an industrial scale.

WO-2004/108658 discloses an alternative process for obtaining (2R,3R)-3-(3-methoxyphenyl)-N,N,2-trimethylpentanamine by converting (2S,3S)-1-(dimethylamino)-3-(3-methoxyphenyl)-2-methyl-3-pentanol into a mixture of (2R,3R) and (2R,3S)-3-(3-methoxyphenyl)-N,N,2-trimethylpentanamine as outlined below.

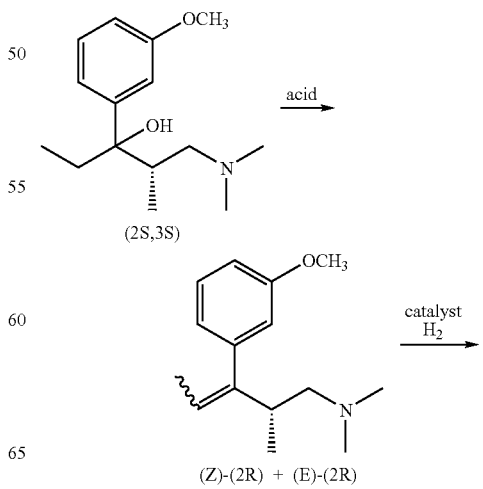

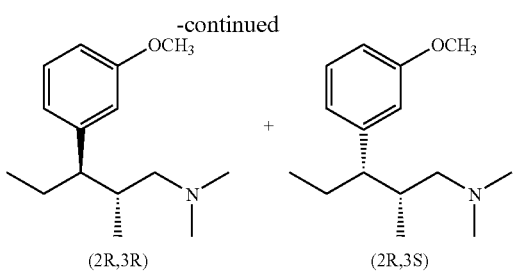

The resulting mixture of (2R,3R) and (2R,3S)-3-(3-methoxyphenyl)-N,N,2-trimethylpentanamine has to be separated into its individual stereoisomers in order to obtain the desired (2R,3R)-3-(3-methoxyphenyl)-N,N,2-trimethylpentanamine, which can then be converted into tapentadol by e.g. heating with concentrated hydrobromic acid as described in EP-A-0,693,475.

WO-2005/000788 discloses an alternative process for obtaining (2R,3R)-3-(3-methoxyphenyl)-N,N, 2-trimethylpentanamine by converting (2S,3S)-1-(dimethylamino)-3-(3-methoxyphenyl)-2-methyl-3-pentanol into a mixture of (2R,3R) and (2R,3S)-3-(3-methoxyphenyl)-N,N,2-trimethylpentanamine as outlined below.

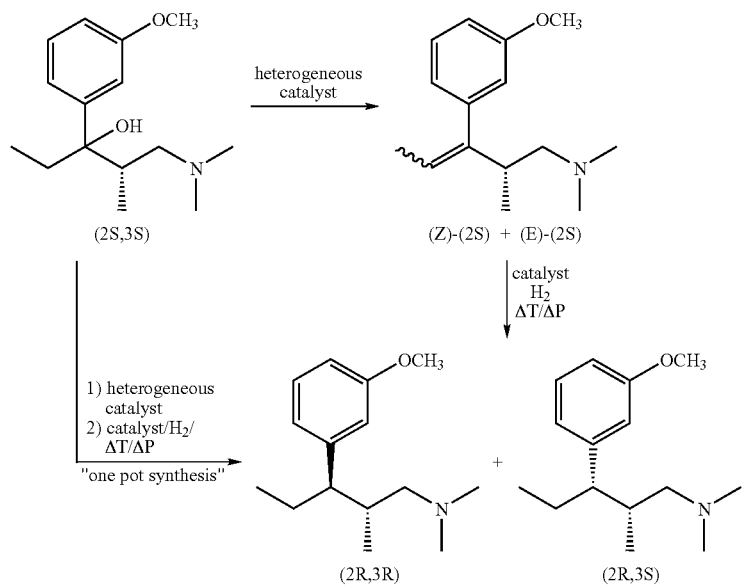

The resulting mixture of (2R,3R) and (2R,3S)-3-(3-methoxyphenyl)-N,N,2-trimethylpentanamine has to be separated into its individual stereoisomers in order to obtain the desired (2R,3R)-3-(3-methoxyphenyl)-N,N,2-trimethylpentanamine, which can then be converted into tapentadol by e.g. heating with concentrated hydrobromic acid as described in EP-A-0,693,475.

Both alternative processes of WO-2004/108658 and WO-2005/00078 have the disadvantage that [3-(3-methoxyphenyl)-N,N,2-trimethylpentanamine is obtained as a mixture of the (2R,3R) and (2R,3S) stereoisomers which have to be separated in order to obtain the desired (2R,3R) stereoisomer. The undesired (2R,3S) stereoisomer cannot be converted into the desired (2R,3R) stereoisomer and has to be disposed of as chemical waste, which is economically undesirable for any industrial scale production.

The object of the present invention is to provide an improved method for the synthesis of (2R,3R)-3-(3-hydroxyphenyl)-N,N,2-trimethylpentanamine which is more convenient and more efficient than the previously known methods.

The present invention achieves this object by providing an improved process for the preparation of (2R,3R)-3-(3-hydroxyphenyl)-N,N,2-trimethylpentanamine, or an acid addition salt thereof.

The present invention relates to a process which is characterized by the steps of a) acylating a compound of formula (VI) wherein R represents $C_{1-6}$alkyl, $C_{3-8}$cycloalkyl, $C_{1-6}$alkylcarbonyl, tetrahydropyranyl, or $C_{1-3}$alkyl substituted with phenyl or naphthyl—with the proviso that R=$CH_3$ is excluded—

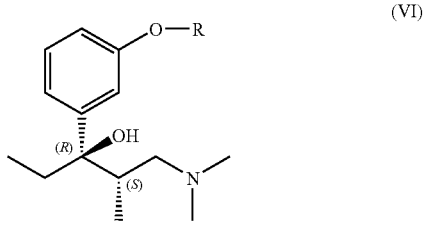

with an acylating agent;

b) stereoselective hydrogenolysis of the thus obtained compound of formula (VII)

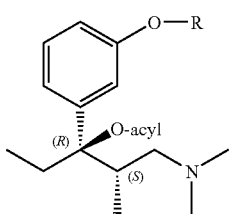

(VII)

using a suitable catalyst in a reaction-inert solvent in the presence of hydrogen resulting in a product VIII, having either $R^1$=H (already deprotected in step b)) or the protection group R is still part of product VIII. In this case ($R^1 \neq H$ in compound VIII) the group R of the obtained compound of formula VIII can be deprotected in a step c)

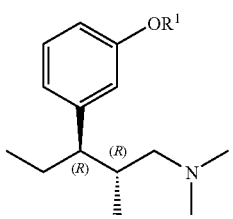

(VIII)

and d) optionally converting the obtained deprotected product into an acid addition salt.

Preferably R represents ethyl, n-propyl, isopropyl, n-butyl, isobutyl, tert-butyl, n-pentyl, n-hexyl, cyclopropyl, cyclobutyl, cyclobutyl, cyclopentyl, cyclohexyl, cycloheptyl, benzyl, phenylethyl, tetrahydropyranyl, —(C=O)—CH$_3$, —(C=O)—CH$_2$CH$_3$, or —(C=O)—C(CH$_3$)$_3$, in the compounds of formula (VI), (VII) and (VIII). More preferably R represents ethyl, cyclopropyl, cyclobutyl, cyclopentyl, cyclohexyl, benzyl, phenylethyl, tetrahydropyranyl or —(C=O)—CH$_3$ in the compounds of formula (VI), (VII) and (VIII). Even more preferably R represents benzyl or tetrahydropyranyl in the compounds of formula (VI), (VII) and (VIII).

For example in case R=benzyl the deprotecting step c) is not necessary, because compound VII is directly transformed in VIII with $R^1$=H via the hydrogenation step. The Benzyl group is very preferred for substitute R, which may be optionally substituted e.g. with halogen substituents or/and nitro-groups.

The acylating agent of step a) is an organic acyl halide or organic acid anhydride selected from acetic anhydride, acetyl chloride, trifluoroacetic anhydride, chloroacetic anhydride, chloro acetylchloride, dichloroacetic anhydride, trichloroacetic anhydride, benzoic anhydride, benzoyl chloride, phthalic anhydride, phtaloyl dichloride, terephthaloyldichloride, succinic anhydride, succinyl chloride, ethyl oxalyl chloride, methyl oxalyl chloride, Meldrum's acid, ethyl chloroformate, methylchloroformate, acetylsalicyloyl chloride, or any other suitable acylating agent.

The catalyst of step b) is selected from a palladium catalyst, or any other suitable catalyst such as e.g. Raney nickel, platinum, platinum on carbon, ruthenium or rhodium on carbon.

The palladium (Pd) catalyst may be a homogeneous Pd catalyst, such as for example Pd(OAc)$_2$, PdCl$_2$, Pd(PPh$_3$)$_4$, Pd(PPh$_3$)$_2$Cl$_2$, Pd$_2$(dba)$_3$ (tris(dibenzylidene acetone)dipalladium), palladium thiomethylphenylglutaramide metallacycle and the like, or a heterogeneous Pd catalyst, such as for example palladium on charcoal, palladium on metal oxides, palladium on zeolites. Preferably, the palladium catalyst is a heterogeneous Pd catalyst, more preferably palladium on charcoal or palladium on carbon (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

The reaction-inert solvent of step b) is selected from diethyl ether, tetrahydrofuran, 2-methyltetrahydrofuran or mixtures thereof.

Preferred agents for deprotecting in step c) are iodotrimethylsilane, sodium ethyl sulphide, lithium iodide, hydrobromic acid; more preferably hydrobromic acid In one embodiment of the present invention, steps a) and b) are executed as a "one pot synthesis" procedure.

The present invention also relates to novel compounds of formula (VII)

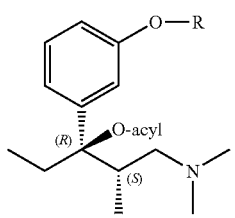

(VII)

The acyl group in compounds of formula (VII) represents CH$_3$—CO—, CF$_3$—CO—, CH$_2$Cl—CO—, CHCl$_2$—CO—, CCl$_3$—CO—, CH$_3$O—CO—CO—, CH$_3$O—CO—, CH$_3$CH$_2$O—CO—, CH$_3$CH$_2$O—CO—CO, phenyl-CO—, or meta-CH$_3$COO-phenyl-CO— when the acylating agent used to prepared the compounds of formula (III) as set out above is selected from acetic anhydride, acetyl chloride, trifluoroacetic anhydride, chloroacetic anhydride, chloro acetylchloride, dichloroacetic anhydride, trichloroacetic anhydride, methyl oxalyl chloride, ethyl oxalyl chloride, methyl chloroformate, ethyl chloroformate, benzoic anhydride, benzoyl chloride, or acetylsalicyloyl chloride. The R group in compounds of formula (VII) represents C$_{1-16}$alkyl, C$_{3-8}$cycloalkyl, C$_{1-6}$alkylcarbonyl, tetrahydropyranyl, or C$_{1-3}$alkyl substituted with phenyl or naphthyl—with the proviso that R=Methyl is excluded—

A preferred embodiment of the invention (R=benzyl) is described in detail exemplarily in the following paragraphs:

The starting material for the process of the present invention, i.e. (2S,3R)-1-(dimethylamino-3-(3-(benzyloxy)phenyl)-)-2-methyl-3-pentanol (compound 4), was prepared by reacting (2S)-3-(dimethylamino)-1-(3-(benzyloxy)phenyl)-2-methyl-1-propanone (compound 3) with ethylmagnesium bromide in THF under Grignard reaction conditions.

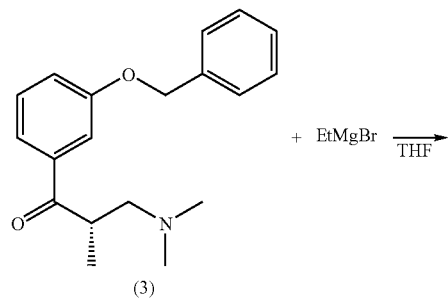

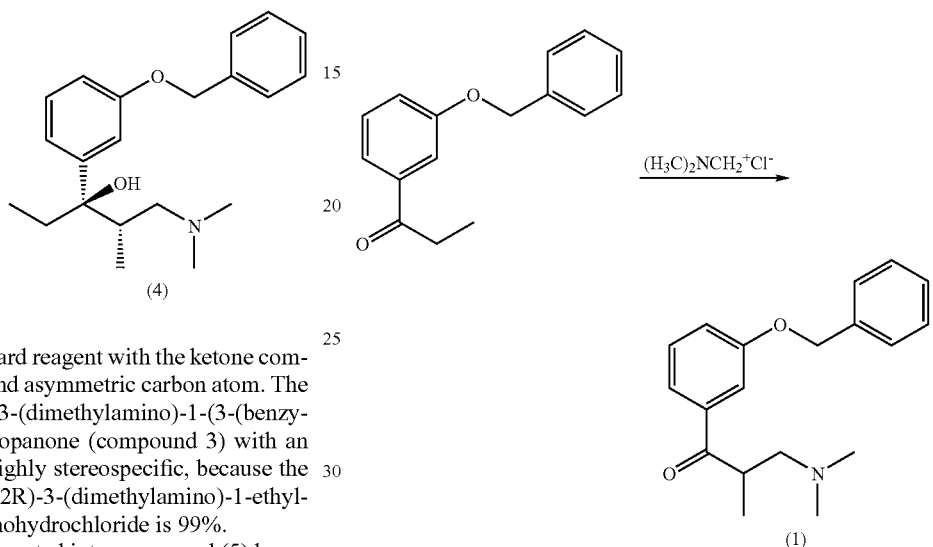

The reaction of the Grignard reagent with the ketone compound (3) introduces a second asymmetric carbon atom. The Grignard reaction of (2S)-3-(dimethylamino)-1-(3-(benzyloxy)phenyl)-2-methyl-1-propanone (compound 3) with an ethylmagnesium halide is highly stereospecific, because the optical purity of the 3-[(1R,2R)-3-(dimethylamino)-1-ethyl-2-methylpropyl]phenol monohydrochloride is 99%.

Compound (4) can be converted into compound (5) by
1.) acylating compound (4) with trifluoroacetic anhydride and
2.) subsequent hydrogenolysis and cleavage of the benzyl ether group over a palladium catalyst using 2-methyltetrahydrofuran as a solvent and
3.), hydrogen chloride as precipitating agent,
in a "one pot synthesis" procedure.

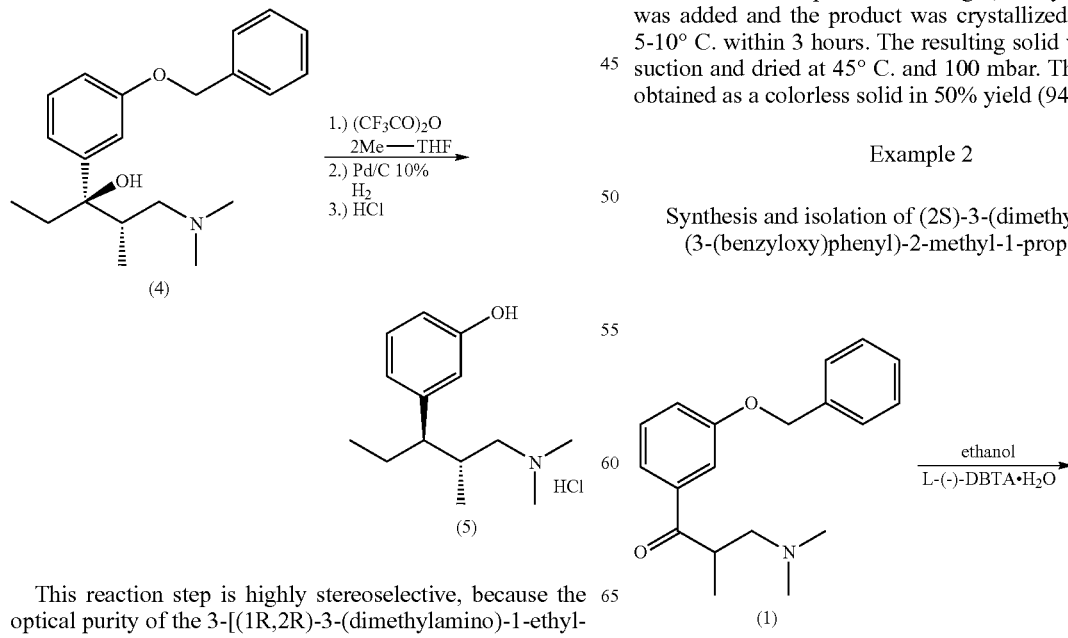

This reaction step is highly stereoselective, because the optical purity of the 3-[(1R,2R)-3-(dimethylamino)-1-ethyl-2-methylpropyl]phenol monohydrochloride is 99%.

The salt formation of compound (5) further improves the optical purity of compound (5).

EXPERIMENTAL PART

Example 1

Synthesis of 3-(dimethylamino)-1-(3-(benzyloxy)phenyl)-2-methyl-1-propanone (1)

At room temperature 1-(3-(benzyloxy)phenyl)propan-1-one (145.0 g; 0.6 mol) was dissolved in acetonitrile (375 ml) in a 500 ml 3 neck-round bottom flask equipped with an over-head stirrer and a thermometer and under stirring N-Methyl-N-methylene-methaneaminium chloride (57.0 g; 0.61 mol) and acetyl chloride (5 ml) were added. After the addition the temperature rose by 10° C. The reaction mixture was stirred at room temperature over night, diethyl ether (375 ml) was added and the product was crystallized by cooling to 5-10° C. within 3 hours. The resulting solid was filtered by suction and dried at 45° C. and 100 mbar. The product was obtained as a colorless solid in 50% yield (94 g).

Example 2

Synthesis and isolation of (2S)-3-(dimethylamino)-1-(3-(benzyloxy)phenyl)-2-methyl-1-propanone (3)

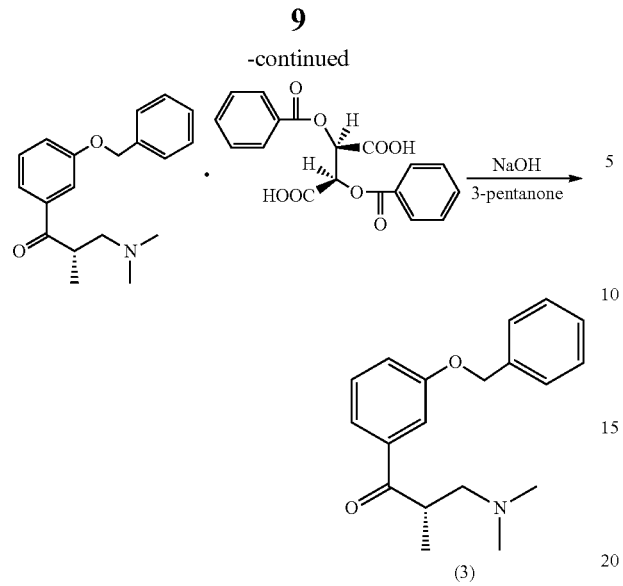

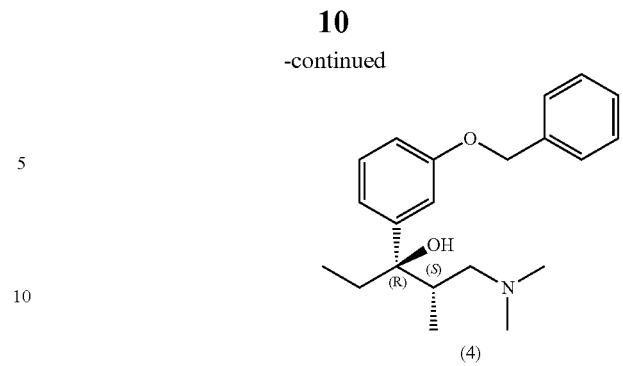

Dibenzoyl tartaric acid monohydrate (78.0 g; 0.2 mol) was dissolved in ethanol abs. (360 ml) by warming to 35-40° C. in a 500 ml reaction vessel equipped with a thermometer. The mixture was cooled to room temperature and added to a solution of (2RS)-3-(dimethylamino)-1-(3-(benzyloxy)phenyl)-2-methyl-1-propanone (1) in ethanol abs. (230 ml). For completion of the crystallization the batch was stirred for 16 hours at 5-8° C. The resulting crystals were filtered off, washed with ethanol and dried at 45° C./100 mbar for 16 hours. The product was obtained as a colourless solid in 65% yield (85.0 g).

(2S)-3-(dimethylamino)-1-(3-(benzyloxy)phenyl)-2-methyl-1-propanone (L)-(−)-dibenzoyl tartrate (85.5 g; 0.13 mol) was dissolved in water in a 1000 ml reaction vessel equipped with a thermometer and 3-pentanone (200 ml) was added. A pH of 12-13 was adjusted with sodium hydroxide aq. (32%; 25 ml; 0.28 mol). The phases were separated and the organic phase was dried over sodium sulfate and the solvent was removed completely in vacuo at 45-50° C. and 5-10 mbar. The product was obtained as an oil in 87% yield (33.6 g). [α]=+17°.

Example 3

Synthesis of (2S,3R)-1-(dimethylamino)-3-(3-(benzoyloxy)phenyl)-2-methyl-3-pentanol (4)

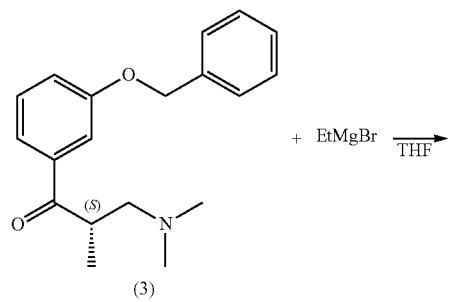

A solution of ethylmagnesiumbromide (1M in THF; 0.15 mol; 150 ml) was charged into a 500 ml 3 necked round-bottom flask with an over-head stirrer, a thermometer, inert gas supply and an addition funnel at 10° C. under nitrogen. To this solution (2S)-3-(dimethylamino)-1-(3-(benzyloxy)phenyl)-2-methyl-1-propanone (3) (33.0 g; 0.11 mol) dissolved in THF (150 ml) was added dropwise at 10-15° C. After the addition was finished the batch was stirred at room temperature for 16 h and quenched with ammonium hydrogensulfate solution (150 ml). The phases were separated and the aqueous phase was re-extracted with 3-pentanone (150 ml). The combined organic phases were dried over sodium sulfate and the solvent was removed completely on the rotary evaporator at 45-50° C. and <10 mbar. A yellowish oil was obtained in 89% yield (32.0 g). [α]=−10.5° C.

Example 4

Synthesis of 3-[(1R,2R)-3-(dimethylamino)-1-ethyl-2-methylpropyl]phenol monohydrochloride (5)

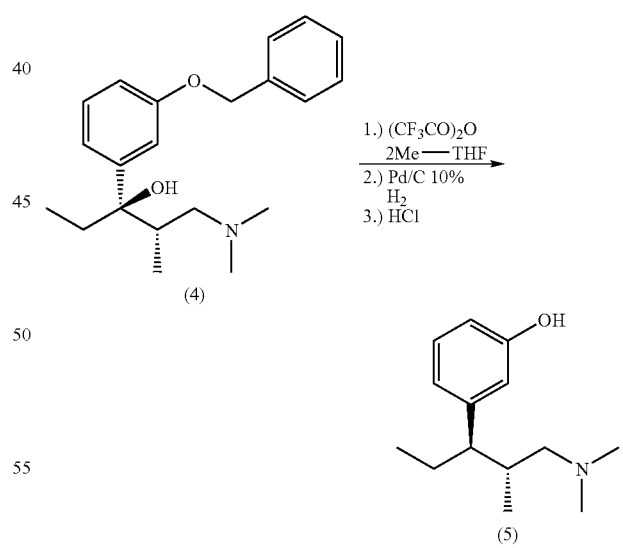

In a standard laboratory vessel equipped with a stirrer and a thermometer (2S,3R)-1-(dimethylamino)-3-(3-(benzyloxy)phenyl)-2-methyl-3-pentanol (4) (21.0 g; 0.064 mol) was dissolved in methyl tetrahydrofurane (125 ml) and trifluoroacetic anhydride (20 g, 0.095 mol) was added. The mixture was warmed to 40-45° C. for four hours under stirring. The mixture was then cooled to room temperature and Pd/C (5%; 2.5 g; 1.9 mol-%) was added under a nitrogen atmosphere.

The mixture was transferred to a hydrogenation apparatus and hydrogenated at 3 bar/800 rpm for 16 hours. The catalyst was filtered off and the resulting solution was cooled to 5-10° C. in an ice bath. Water (1.1 g; 0.06 mol) was added and Trimethylchlorosilane (6.95 g; 0.064 mol) was added dropwise. For crystallization the mixture was stirred at 5-8° C. for 16 hours. The crystals were filtered off, washed with acetone and dried in the drying oven at 40-45° C. and 100 mbar for 16 hours. The product was obtained as a colorless crystalline solid in 89% yield (14.7 g; m. p. 201° C., enantiomeric purity: 99%, purity: 97.7%; (HPLC); assay: 95.5% (HPLC)).

Compound (5) prepared according to the procedure of Example 5 comprises 96.9% of the desired (2R,3R) enantiomer, 1% of the (2S,3S) enantiomer and 2.1% of the (2R,3S) enantiomer.

The invention claimed is:

1. A process for preparing a compound corresponding to formula (VIII):

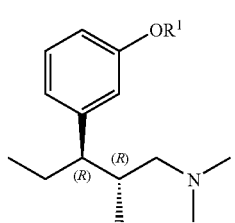

(VIII)

wherein
R$^1$ represents H, C$_{3-8}$ cycloalkyl, C$_{1-6}$ alkylcarbonyl, tetrahydropyranyl, or C$_{1-3}$ alkyl substituted with phenyl or naphthyl;
or an acid addition salt thereof, said process comprising:
a) acylating a compound corresponding to formula (VI):

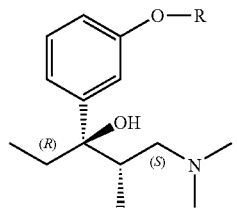

(VI)

wherein
R represents C$_{3-8}$cycloalkyl, C$_{1-6}$alkylcarbonyl, tetrahydropyranyl, or C$_{1-3}$alkyl substituted with phenyl or naphthyl;
with an acylating agent to yield a compound corresponding to formula (VII):

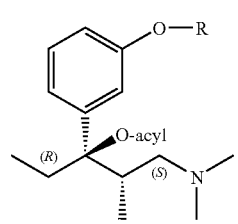

(VII)

b) hydrogenolyzing the compound of formula (VII) using a catalyst in an inert solvent in the presence of hydrogen to yield a compound of formula (VIII);
c) if R$^1$≠H, optionally deprotecting the group R$^1$ of formula (VIII); and
d) optionally converting the compound of formula (VIII) into an acid addition salt.

2. A process according to claim 1, wherein the acylating agent is an organic acyl halide or organic acid anhydride.

3. A process according to claim 1, wherein the acylating agent is selected from the group consisting of trifluoroacetic anhydride, chloroacetic anhydride, chloro acetylchloride, dichloroacetic anhydride, trichloroacetic anhydride, benzoic anhydride, benzoyl chloride, phthalic anhydride, phtaloyl dichloride, terephthaloyldichloride, succinic anhydride, succinyl chloride, ethyl oxalyl chloride, methyl oxalyl chloride, Meldrum's acid, ethyl chloroformate, methylchloroformate, and acetylsalicyloyl chloride.

4. A process according to claim 3, wherein the acylating agent is trifluoroacetic anhydride.

5. A process according to claim 1, wherein said catalyst is selected from the group consisting of Raney nickel, palladium, palladium on carbon, platinum, platinum on carbon, ruthenium, and rhodium on carbon.

6. A process according to claim 5, wherein the catalyst is palladium on carbon.

7. A process according to claim 1, wherein said inert solvent is selected from the group consisting of diethyl ether, tetrahydrofuran, 2-methyltetrahydrofuran, and mixtures thereof.

8. A process according to claim 1, wherein R represents cyclopropyl, cyclobutyl, cyclobutyl, cyclopentyl, cyclohexyl, cycloheptyl, benzyl, phenylethyl, tetrahydropyranyl, —(C=O)—CH$_3$, —(C=O)—CH$_2$CH$_3$, or —(C=O)—C(CH$_3$)$_3$.

9. A process according to claim 8, wherein R represents benzyl.

10. A process according to claim 9, wherein (2R,3R)-3-(3-hydroxyphenyl)-N,N,2-trimethylpentanamine is converted into its corresponding hydrochloric acid addition salt.

11. A process according to claim 1, wherein the acylating and hydrogenolysis are carried out in a one-pot reaction.

12. A compound corresponding to formula (VII):

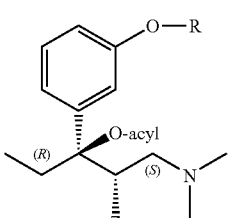

(VII)

wherein
R represents C$_{3-8}$ cycloalkyl, C$_{1-6}$ alkylcarbonyl, tetrahydropyranyl, or C$_{1-3}$ alkyl substituted with phenyl or naphthyl.

13. A compound as claimed in claim 12, wherein acyl represents CF$_3$—CO—, CH$_2$Cl—CO—, CHCl$_2$—CO—, CCl$_3$—CO—, CH$_3$O—CO—, CH$_3$CH$_2$O—CO—, CH$_3$O—CO—CO—, CH$_3$CH$_2$O—CO—CO—, phenyl-CO—, or meta-CH$_3$COO-phenyl-CO—.

14. A compound as claimed in claim 13, wherein R represents cyclopropyl, cyclobutyl, cyclobutyl, cyclopentyl, cyclohexyl, cycloheptyl, benzyl, phenylethyl, tetrahydropyranyl, —(C=O)—CH$_3$, —(C=O)—CH$_2$CH$_3$, or —(C=O)—C(CH$_3$)$_3$.

15. A compound as claimed in claim 14, wherein acyl represents CF$_3$—CO—, and R represents benzyl.

\* \* \* \* \*